United States Patent

Karrer et al.

[11] 4,057,587
[45] Nov. 8, 1977

[54] DIPHENYL ETHER DERIVATIVES

[75] Inventors: Friedrich Karrer, Basel; Saleem Farooq, Aesch, both of Switzerland

[73] Assignee: Ciba-Geigy Corporation, Ardsley, N.Y.

[21] Appl. No.: 623,877

[22] Filed: Oct. 20, 1975

[30] Foreign Application Priority Data

Oct. 24, 1974 Switzerland .......... 14247/74
Sept. 18, 1975 Switzerland .......... 12297/75

[51] Int. Cl.² ........................... C07C 43/22
[52] U.S. Cl. .................. 260/613 R; 424/350
[58] Field of Search .................... 260/613 R

[56] References Cited

U.S. PATENT DOCUMENTS

| | | | |
|---|---|---|---|
| 3,131,166 | 4/1964 | Harris et al. | 260/613 R X |
| 3,240,703 | 3/1966 | Lombard et al. | 252/45.7 |
| 3,340,308 | 9/1967 | Sterling et al. | 260/613 R |
| 3,600,437 | 8/1971 | Marshall | 260/613 R X |
| 3,963,786 | 6/1976 | Karrer et al. | 260/613 R |

Primary Examiner—Bernard Helfin
Attorney, Agent, or Firm—Harry Falber

[57] ABSTRACT

New compounds of the formula

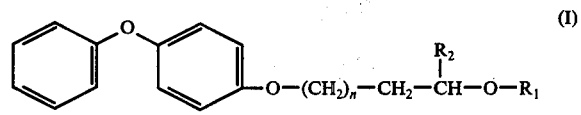

(I)

wherein
$R_1$ represents a $C_3$–$C_5$-alkenyl, $C_3$–$C_5$-halogenoalkenyl or $C_3$–$C_5$-alkynyl radical,
$R_2$ represents a hydrogen atom or a methyl radical, and
$n$ represents the number 1 or 2, which compounds are effective against pests, processes for their production, compositions containing the same and a method of combatting pests are described.

7 Claims, No Drawings

DIPHENYL ETHER DERIVATIVES

The present invention relates to new 4-substituted diphenyl ether derivatives which are effective against pests, to processes for their production, as well as to compositions and processes for the control of pests by use of the new derivatives as active substances.

The new compounds of the invention correspond to the formula I

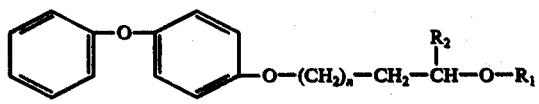

wherein
- $R_1$ represents a $C_3$-$C_5$-alkenyl, $C_3$-$C_5$-halogenoalkenyl or $C_3$-$C_5$-alkynyl radical,
- $R_2$ represents a hydrogen atom or a methyl radical, and
- $n$ represents the number 1 or 2.

Alkenyl, halogenoalkenyl and alkynyl radicals denoted by $R_1$ can be branched-chain or straight-chain. Alkenyl and halogenoalkenyl radicals are, e.g., the allyl, 1-methylallyl, 2-methylallyl, 3-methylallyl and 1,2-dimethylallyl radical, as well as their halogen-substituted derivatives, i.e. chlorine-, fluorine, bromine- and iodine-substituted derivatives, such as the 1-chloroallyl, 3-chloroallyl, 3-bromoallyl, 3-fluoroallyl, 3-iodoallyl, 3-chloromethylallyl and 1-methyl-3-chloroallyl radical. Suitable alkynyl radicals to be mentioned are, inter alia, the propargyl, but-3-in-2-yl and 2-methyl-but-3-in-2-yl radical.

Compounds of the above-mentioned formula I that are of particular importance on account of their action on pests, especially on insects, in particular on larvae and pupae of insects, and on members of the order Acarina, are those wherein
- $R_1$ represents a $C_3$-$C_5$-alkenyl, $C_3$-$C_5$-halogenoalkenyl or $C_3$-$C_5$-alkynyl radical,
- $R_2$ represents a hydrogen atom or a methyl radical, and
- $n$ represents the number 1.

And preferred compounds among these are those wherein
- $R_1$ represents an allyl, 2-chloroallyl, propargyl or 4-pentinyl radical.

Compounds of this type are, for example, those for which the substituents $R_1$ and $R_2$ as well as $n$ have the following meanings:

| $R_1$ | $R_2$ | n |
|---|---|---|
| $CH_2=CH-CH_2-$ | $CH_3-$ | 1 |
| $Cl-CH=CH-CH_2-$ | $CH_3-$ | 1 |
| $CH\equiv C-CH(CH_3)-$ | $CH_3-$ | 1 |
| $CH\equiv C-CH_2-$ | H | 1 |
| $CH_2=CH-CH_2-$ | H | 2 |
| $Cl-CH=CH-CH_2-$ | H | 1 |
| $CH\equiv C-CH_2-$ | H | 2 |
| $CH\equiv C-CH(CH_3)-$ | H | 2 |
| $CH_2=CH-CH_2-$ | $CH_3-$ | 1 |
| $CH\equiv C-CH_2-CH_2-CH_2-$ | H | 1 |

The new compounds of the formula I are advantageously obtained by methods known per se; for example, by a process wherein a. a compound of the formula II

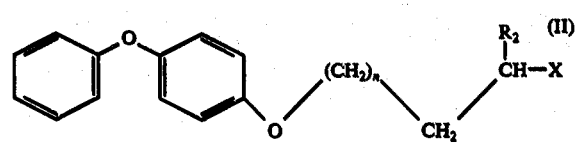

is reacted with a compound of the formula III

b. a compound of the formula IV

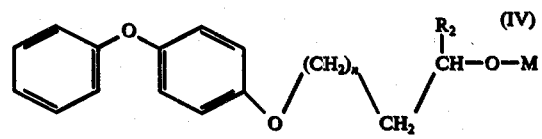

is reacted with a compound of the formula V

or c. a compound of the formula VI

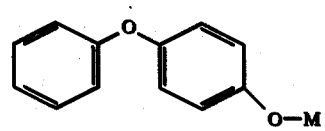

is treated with a compound of the formula VII

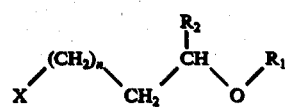

in which formulae II to VII the symbols have the following meanings:

M stands for a metal ion of the main group I or II of the periodic system, particularly for a sodium, potassium or lithium ion, X represents a halogen atom, especially a chlorine or bromine atom, and $R_1$, $R_2$ and $n$ have the meanings given already under formula I.

Depending on the reactivity of the applied halide of the formulae II, V and VII, these processes can be performed in various solvents and at different reaction temperatures, preferably in the presence of at least one mole of a base.

Suitable solvents are, in particular, 1,2-dimethoxyethane, tetrahydrofuran, dioxane, dialkyl ether, dimethylformamide, dimethylsulphoxide, hexamethylphosphoric acid triamide and sulpholane. It is however possible to use other solvents. Examples of suitable bases are alkali metal hydroxides, alkali metal carbonates and alkali metal hydrides, as well as alkali metal alkoxides. The reaction temperatures for processes (a) and (b) are between 0° and 100° C, mostly between 10° and 80° C, and for process (c) between room temperature and 120° C, usually between 20° and 100° C.

The reactions in certain cases can advantageously be carried out in a protective gas atmosphere, e.g. in a nitrogen atmosphere.

The starting materials of the formulae III and V to VII are known from the literature, while those of the formulae II and IV are easily obtainable from known intermediates, e.g. by a. reaction of a compound of the above mentioned formula VI in the presence of a solvent, such as acetone, with a halide of the formula VIII $$X-(CH_2)_n-CH=CH-R_2 \quad \text{(VIII)}$$

wherein X represents a halogen atom, preferably a chlorine or bromine atom; reaction of the resulting reaction product of the formula IX $$\text{(IX)}$$

with water in the presence of a mercury(II)-salt, especially mercury(II)-acetate or mercury(II)-trifluoroacetate, to give a compound of the formula (X)

$$\text{(X)}$$

and subsequent treatment of this compound, for example with an alkali metal hydride, in the presence of tetrahydrofuran and/or hexamethylphosphoric acid triamide, as a result of which there is formed a compound of the formula IV above, wherein M represents an alkali metal ion; or b. reaction of a compound of the previously given formula VI with a dihalide of the formula XI $$X-(CH_2)_n-CH_2-CH_2-X \quad \text{(XI)}$$

wherein X represents a halogen atom, preferably a chlorine or bromine atom, to obtain a compound of the formula II wherein $R_2$ stands for a hydrogen atom.

Compounds of the formula I wherein $R_2$ represents a methyl radical can be present in different optically active isomers. If therefore in such cases in the production process no optically active starting materials are used, then there are necessarily obtained racemic mixtures. Also cis/trans mixtures of isomers are obtainable if $R_1$ denotes a substituted alkenyl radical, e.g. a halogenoallyl radical.

The various mixtures of isomers can be separated into the isomeric forms, e.g., by means of chromatographical separation methods, e.g. by adsorption on a separating material having selective adsorption activity, such as silica gel or aluminium oxide, and subsequent elution of the separated isomers with a suitable solvent, e.g. diethyl ether, hexane, methyl acetate or ethyl acetate, etc.. A further chromatographical separation method is gas chromatography. In certain cases, a mixture of isomers can be separated also by fractional distillation or fractional crystallisation.

It is understood that the present invention embraces both specific sterioisomers or cis/trans isomers and the nonseparated mixtures thereof.

The active substances of the formula I are suitable for the control of pests, particularly for the control of insects in fruit growing, especially on citrus fruit, and on cotton plants and in forests, as well as for the control of pests affecting hygiene. These active substances can be applied, in particular, to control the eggs, larvae and pupae of insects, and members of the order Acarina.

Examples of families of insects and Acarina against which the active substances of the formula I have a positive effect are:

Insects

Acrididae, Blattidae, Gryllidae, Gryllotalpidae, Tettigoniidae, Cimicidae, Pyrrhocoridae, Reduviidae, Aphididae, Delphacidae, Diaspididae, Pseudococcidae, Chrysomelidae, Coccinellidae, Bruchidae, Scarabaeidae, Dermestidae, Tenebrionidae, Curculionidae, Tineidae, Noctuidae, Lymantriidae, Pyralidae, Galleridae, Culicidae, Tipulidae, Stomoxydae, Muscidae, Calliphoridae, Trypetidae and Pulicidae;

Acarina

Ixodidae, Argasidae, Tetranychidae and Dermanyssidae.

Other biocidal active substances or compositions may be added to the described compositions of the invention. For the widening of their range of action, the new compositions can contain, in addition to the stated compounds of the general formula I, for example: insecticides, fungicides, bactericides, fungistatics, bacteriostatics or nematocides.

Mention is to be made also of the fact that the compounds of formula I have a low toxicity of warm-blooded animals.

The compounds of formula I can be used on their own or together with suitable carriers and/or additives. Suitable carriers and additives may be solid or liquid, and they correspond to the substances common in formulation practice, such as natural and regenerated substances, solvents, dispersing agents, wetting agents, adhesives, thickeners, binders and/or fertilisers.

For application, the compounds of formula I can be processed into the form of dusts, emulsion concentrates, granulates, dispersions, sprays or solutions, the formulation of these preparations being effected in a manner commonly known in practice.

The compositions according to the invention are produced in a manner known per se by the intimate mixing and/or grinding of active substances of formula I with suitable carriers, optionally with the addition of dispersing agents or solvents that are inert to the active substances. The active substances can be obtained and used in the following forms:

solid preparations: dusts, scattering agents or granulates (coated granulates, impregnated granulates and homogeneous granulates);

liquid preparations:
  a. water-dispersible active-substance concentrates: wettable powders, pastes or emulsions,
  b. solutions: aerosols.

The active substances of formula I can be formulated, for example, as follows (parts denote parts by weight):

Dusts

The following substances are used to produce (a) to 5% dust, and (b) a 2% dust:

a.

5 parts of active substance,
95 parts of talcum;

b.

2 parts of active substance,
1 part of highly dispersed silicic acid,
97 parts of talcum.

The active substances are mixed and ground with the carriers.

Granulate

The following substances are used to produce a 5% granulate:
5 parts of active substance,
0.25 part of epichlorohydrin,
0.25 part of cetyl polyglycol ether,
3.50 parts of polyethylene glycol,
91 parts of kaolin (particle size 0.3–0.8 mm).

The active substance is mixed with epichlorohydrin and dissolved with 6 parts of acetone; the polyethylene glycol and cetyl polyglycol ether are then added. The solution thus obtained is sprayed on to kaolin, and the acetone is subsequently evaporated off in vacuo.

Wettable powder

The following constituents are used in the preparation of (a) a 40%, (b) and (c) a 25%, and (d) a 10% wettable powder:

a.

40 parts of active substance,
5 parts of sodium lignin sulphonate,
1 part of sodium dibutyl-naphthalene sulphonate,
54 parts of silicic acid;

b.

25 parts of active substance,
4.5 parts of calcium lignin sulphonate,
1.9 parts of Champagne chalk/hydroxyethyl cellulose mixture (1:1),
1.5 parts of sodium dibutyl naphthalene sulphonate,
19.5 parts of silicic acid
19.5 parts of Champagne chalk,
28.1 parts of kaolin;

c.

25 parts of active substance, 2.5 parts of isooctylphenoxy-polyoxyethylene-ethanol,
1.7 parts of Champagne chalk/hydroxyethyl cellulose mixture (1:1),
8.3 parts of sodium aluminium silicate,
16.5 parts of kieselguhr,
46 parts of kaolin;

d.

10 parts of active substance,
3 parts of a mixture of the sodium salts of saturated fatty alcohol sulphates,
5 parts of naphthalenesulphonic acid/formaldehyde condensate,
82 parts of kaolin.

The active substances are intimately mixed, in suitable mixers, with the additives; the mixture is then ground in the appropriate mills and rollers. Wettable powders are obtained which can be diluted with water to give suspensions of any desired concentration.

Emulsifiable Concentrates

The following substances are used to produce (a) a 10% (b) a 25% and (c) a 50% emulsifiable concentrate:

a.

10 parts of active substance,
3.4 parts of epoxidised vegetable oil,
3.4 parts of a combination emulsifier consisting of fatty alcohol polyglycol ether and alkylarylsulphonate calcium salt,
40 parts of dimethylformamide,
43.2 parts of xylene;

b.

25 parts of active substance,
2.5 parts of epoxidised vegetable oil,
10 parts of alkylarylsulphonate/fatty alcohol-polyglycol ether mixture,
5 parts of dimethylformamide,
57.5 parts of xylene;

c.

50 parts of active substance,
4.2 parts of tributylphenol-polyglycol ether,
5.8 parts of calcium-dodecylbenzenesulphonate,
20 parts of cyclohexanone,
20 parts of xylene.

It is possible to prepare from these concentrates, by dilution with water, emulsions of any desired concentration.

Spray

The following constituents are used to produce (a) a 5% spray and (b) a 95% spray:

a.

5 parts of active substance,
1 part of epichlorohydrin,
94 parts of ligroin (boiling limits 160°–190° C);

b.

95 parts of active substance,
5 parts of epichlorohydrin.

The following Examples serve to further illustrate the invention.

EXAMPLE 1

A. Production of
1-(4-phenoxy)-phenoxy-3-propargyloxybutane of the formula

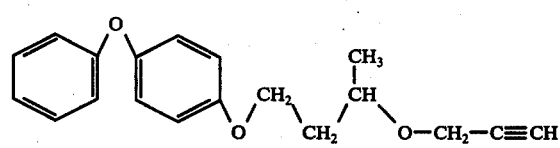

3.2 g of sodium hydride dispersion in mineral oil (60% NaH) was repeatedly washed with hexane and tetrahydrofuran, and then covered over with 60 ml of pure tetrahydrofuran and 60 ml of hexamethylphosphoric acid triamide. To this suspension under an N₂ protective gas atmosphere there are afterwards added dropwise, in the course of one hour, the solution of 20.6 g of 1-(4-phenoxy)-phenoxybutan-3-ol in 20 ml of tetrahydrofuran, and the mixture was subsequently heated with continuous stirring for 5 hours at 40°-45° C. There was thereupon added dropwise to the reaction mixture with ice cooling (internal temperature about 5° C), within one hour, 14.5 g of propargyl bromide and stirring was maintained for a further 15 hours at room temperature.

In further processing, the tetrahydrofuran was extensively distilled off in vacuo at a maximum temperature of 35° C. The reaction mixture was subsequently poured into 600 ml of ice water, and extraction with ether was repeatedly carried out. The combined ether phases were repeatedly washed with saturated sodium chloride solution, dried over sodium sulphate and freed from the solvent. The oily residue was chromatographed on silica gel for further purification (eluant: diethyl ether/-hexane 1:4) to obtain 1-(4-phenoxy)-phenoxy-3-propargyloxy-butane (Compound No. 1); refractive index of the product: $n_D^{20}$: 1.5510.

B. Production of the starting product: 1-(4-phenoxy)-phenoxy-butan-1-ol

The solution of 38 g of 1-(4-phenoxy)-phenoxy-2-butene (m.p. 43°-44° C) in 140 ml of pure tetrahydrofuran was added dropwise in the course of 30 minutes at room temperature, with stirring, to a solution of 63.6 g of mercury(II)-acetate in 200 ml of water. The resulting yellow emulsion was stirred for a further 7 hours at room temperature. The reaction mixture was then cooled to 0° C, and there were added dropwise, within about 15 minutes, 200 ml of 3N sodium hydroxide solution with subsequently within about 40 minutes, likewise at 0°-5° C, 200 ml of a 0.5N sodium borohydride solution in 3N sodium hydroxide solution. The reaction mixture was afterwards stirred for a further 18 at room temperature.

In further processing, the reaction solution was decanted from the quantitively precipitated metallic mercury and repeatedly washed with ether. The combined ether phases, after repeated washing with saturated sodium chloride solution, were dried over sodium sulphate and freed from the solvent in vacuo. The residue, solidifying largely in crystalline form, was further purified by chromatography on silica gel (eluant: methyl acetate/hexane 2:3) to obtain pure 1-(4-phenoxy)-phenoxy-butan-3-ol, m.p. 43°-45° C.

EXAMPLE 2

The following compounds of the formula I were produced in a manner analogous to that of Example 1 A:

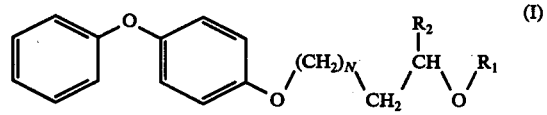

(cis/trans mixtures of isomers indicated by asterisks).

| Comp. No. | $R_1$ | $R_2$ | n | Physical data |
|---|---|---|---|---|
| 2 | CH$_2$=CH—CH$_2$— | CH$_3$— | 1 | $n_D^{20}$: 1,5429 |
| 3 | CH≡C—CH$_2$— | H | 1 | 1,5588 |
| 4 | CH$_2$=CH—CH$_2$— | H | 2 | 1,5431 |
| 5 | Cl—CH=CH—CH$_2$— | H | 1 | 1,5612 |
| 6 | CH≡C—CH$_2$— | H | 2 | 1,5513 |
| 7 | CH$_2$=CH—CH$_2$— | CH$_3$— | 1 | 1,5429 |
| 8 | CH≡C—CH$_2$—CH$_2$—CH$_2$— | H | 1 | 1,5498 |

EXAMPLE 3

A. Contact action on Dysdercus-fasciatus larvae

A specific amount of a 0.1% acetonic active-substance solution (corresponding to 10 mg of active substance per square meter) was transferred by pipet to an aluminium dish and uniformly distributed. After evaporation of the acetone, 10 larvae in the 5th stage of Dysdercus fasciatus were placed into the treated dish containing feed and moist cotton wool. The dish was then covered with a perforated lid. After about 10 days, i.e. as soon as the control insects had moulted into adults, the test insects were examined to determine the number of normal adults.

Compounds according to Examples 1 and 2 exhibited a good action in the above test.

B. Contact action on *Aedes-aegypti larvae*

About 20 two-day-old larvae of the yellow-fever mosquito (*Aedes aegypti*) were placed in position in a beaker containing a solution of the active substance (concentration 5 ppm). The beaker was then covered with a perforated lid. After the control insects had moulted into adults, the test insects were examined and the percentage of normal adults in comparison with the control adults was determined.

Compounds according to Examples 1 and 2 exhibited a good action in the above test.

C. Contact action on *Tenebrio-molitor pupae*

A specific amount of a 0.1% acetonic active-substance solution corresponding to 10 mg of active substance per square meter was transferred by pipet into an aluminium dish and uniformly distributed. After evaporation of the acetone, 10 freshly formed pupae were placed onto the threaded surface, and the dish was covered with a perforated lid. After the control insects had left the cocoon as imagines, the test insects were examined to determine the number of normal adults.

Compounds according to Examples 1 and 2 exhibited a good action in the above test.

EXAMPLE 4

A. Action against *Musca domestica*

An amount in each case of 50 g of CSMA maggot substrate was weighed off in beakers. For each active substance, 2.5 ml of a 1% acetonic solution of the respective substance was transferred by pipet twice of 50 g of maggot substrate each time. After a thorough mixing of the treated substrate, the solvent was allowed to evaporate off. There were then deposited per active substance in each case 25 one-, two- and three-day-old maggots and about 50 fly eggs. After completion of pupation, the pupae were flushed out and counted. After a period of ten days, the number of emerged flies was counted and hence any effect on metamorphosis was established.

Compounds according to Examples 1 and 2 exhibited in this test a good action on *Musca domestica*.

B. Action against *Ephestia kuhniella*

50 g of wheat flour was made up in two beakers with a specific amount of active substance to give a 5% dust, the concentration being 0.5%. Into each beaker (25 g of flour) there were placed 10 larvae of Ephesta kuhniella. The pattern of population was ascertained over a period of 8 weeks and the number of moths determined.

Compounds according to Examples 1 and 2 exhibited in this test a good action on Ephestia kuhniella.

EXAMPLE 5

Action against red spider mites

Phaseolus vulgaris (bush beans) were infested, 12 hours before the test for acaricidal action, with an infested piece of leaf from a mass culture of Tetranychus urticae. The transferred mobile stages were sprayed with the emulsified test preparations, at a concentration of 0.04%, by means of a chromatography-sprayer in a manner ensuring no running-off of the spray liquor. An assessment was made after 2 to 7 days, by examination under a binocular, of the living and of the dead larvae, adults and eggs, and the results were expressed in percentages. The treated plants were kept during the holding time in greenhouse compartments at 25° C.

Compounds according to Examples 1 and 2 exhibited in the above test a good action against eggs, larvae and adults of *Tetranychus uritcae*.

We claim:

1. A compound of the formula I

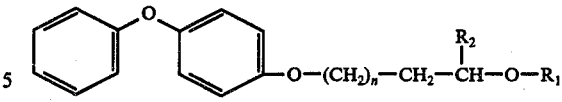

wherein
  $R_1$ represents a $C_3-C_5$-alkenyl, $C_3-C_5$-halogenoalkenyl or $C_3-C_5$-alkynyl radical,
  $R_2$ represents a hydrogen atom or a methyl radical, and
  $n$ represents the number 1 or 2.

2. The compound according to claim 1 wherein $n$ represents the number 1.

3. The compound according to claim 2 wherein $R_1$ represents an allyl, 3-chloroallyl, propargyl or 4-pentinyl radical.

4. 1-(4-Phenoxy)-phenoxy-3-propargyloxy-butane.

5. 1-(4-Phenoxy)-phenoxy-3-propargyloxy-propane.

6. 1-(4-Phenoxy)-phenoxy-3-allyloxy-butane.

7. 1-(4-Phenoxy)-phenoxy-3-(3-chloroallyloxy)-propane.

* * * * *